(12) United States Patent
Rashid

(10) Patent No.: US 11,051,974 B2
(45) Date of Patent: Jul. 6, 2021

(54) FLUENCY AID

(71) Applicant: Cirrus Logic International Semiconductor Ltd., Edinburgh (GB)

(72) Inventor: Tahir Rashid, Tewkesbury (GB)

(73) Assignee: Cirrus Logic, Inc., Austin, TX (US)

( * ) Notice: Subject to any disclaimer, the term of this patent is extended or adjusted under 35 U.S.C. 154(b) by 106 days.

(21) Appl. No.: 16/261,038

(22) Filed: Jan. 29, 2019

(65) Prior Publication Data

US 2019/0231586 A1    Aug. 1, 2019

Related U.S. Application Data

(60) Provisional application No. 62/624,445, filed on Jan. 31, 2018.

(30) Foreign Application Priority Data

Mar. 15, 2018   (GB) ..................................... 1804170

(51) Int. Cl.
*A61F 5/58* (2006.01)
*G10L 21/0208* (2013.01)
*A61B 5/12* (2006.01)
*G10L 21/003* (2013.01)
*G10L 21/057* (2013.01)

(52) U.S. Cl.
CPC ................ *A61F 5/58* (2013.01); *A61B 5/121* (2013.01); *G10L 21/003* (2013.01); *G10L 21/0208* (2013.01); *G10L 2021/0575* (2013.01)

(58) Field of Classification Search
None
See application file for complete search history.

(56) References Cited

U.S. PATENT DOCUMENTS

| | | | | |
|---|---|---|---|---|
| 3,773,032 A | * | 11/1973 | Donovan | A61B 5/121 600/23 |
| 5,794,203 A | * | 8/1998 | Kehoe | A61F 5/58 704/271 |
| 2007/0049788 A1 | * | 3/2007 | Kalinowski | A61F 5/58 600/23 |

OTHER PUBLICATIONS

Combined Search and Examination Report under Sections 17 and 18(3), UKIPO, Application No. GB1804170.7, dated Sep. 3, 2018.
Examination Report under Section 18(3), UKIPO, Application No. GB1804170.7, dated Sep. 22, 2020.

* cited by examiner

*Primary Examiner* — Antim G Shah
(74) *Attorney, Agent, or Firm* — Jackson Walker L.L.P.

(57) ABSTRACT

The present disclosure relates to a fluency aid comprising: a pacing signal generator operable to output a signal for generating, at regular time intervals, an audible sound; and a controller operable, in response to a voice being detected by a voice detector, to control the pacing signal generator such that the output signal causes the audible sound to continue, stop or fade.

10 Claims, 3 Drawing Sheets

FLUENCY AID

The present disclosure claims priority to U.S. Provisional Patent Application Ser. No. 62/624,445, filed Jan. 31, 2018, and United Kingdom Patent Application No. 1804170.7, filed Mar. 15, 2018, each of which is incorporated by reference herein in its entirety.

TECHNICAL FIELD

The present disclosure relates to a fluency aid, and in particular to a fluency aid for use by persons suffering from a stammer or other speech-related conditions to aid fluency of speaking.

BACKGROUND

Stammering affects about 1-3% of the world's population. From historical records available it is suggested that the condition has always affected 1-3% of the population and is agnostic of race, religion, wealth, and upbringing. Many with the condition are misjudged by the way they talk and as a result many are treated differently in society and may fail to fulfil their potential. The situation can be particularly difficult for children and young adults who may be bullied or ridiculed at school and may find themselves withdrawing from society at a time when they should be finding their place in the world. The condition leaves many feeling anxious and isolated.

There are a number of known auditory effects that can help alleviate stammering. Electronic devices have in the past been created to utilise these effects to help give stammerers greater fluency. Many of these devices are large and cumbersome and cannot be used without attracting further ridicule. More discrete devices still resemble medical devices and their cost puts them out of the reach of most stammerers.

Stammering and stuttering refer to the same condition, with the term stammer being used more in the UK and stutter being used more in the USA. The exact cause of stammering is unknown although it is now generally accepted that it is the result of the brain's neural circuits that control speech having been 'mis-wired'.

It is desirable to provide a device capable of aiding fluency in a person suffering from a stammer, by improving control of auditory feedback to the user.

STATEMENTS OF INVENTION

According to an example of a first aspect of the present disclosure there is provided a fluency aid comprising: a pacing signal generator operable to output a signal for generating, at regular time intervals, an audible sound; and a controller operable, in response to a voice being detected by a voice detector, to control the pacing signal generator such that the output signal causes the audible sound to continue, stop or fade.

Speaking to a timed rhythm has the benefit of improving fluency in many stammerers. The fluency aid of the present disclosure includes a pacing signal generator. The pacing signal generator is able to output a signal for generating an audible sound. The audible sound is output at regularly timed intervals to allow the user to speak with a regular rhythm. Based on a voice being detected by a voice detector, a controller is operable to control the pacing signal generator so that the output signal causes the audible sound to continue, stop or fade. The pacing signal generator may for example be a computer processor. The pacing signal generator may also include a timer, for setting a preferred amount of time for the audible sound to be output, and/or a speaker, for outputting the audible sound.

The user may prefer the audible sound to continue being output at regularly timed intervals even when the user is speaking. Alternatively, a user may prefer that the audible sound continues, but is faded either completely or partially, to allow the user to hear themselves speak over the audible sound. Further still, some users may only require the regularly timed audible sound to help them start speaking and therefore the controller may perform control so that the audible sound stops.

A voice detector may for example be or may comprise a microphone. In addition, the voice detector may comprise signal processing operations which allow speech-like sounds to be identified. Thus, according to one example, sounds which are detected by the microphone of the voice detector will be converted into digital form for use by parts which implement digital signal processing operations upon signals that are derived from the microphone.

The voice detector may preferably be positioned, in use, so as to be in a speech region in front of a user's mouth. Positioning the voice detector in the speech region in front of a user's mouth provides the advantage that the voice detector may detect the user's voice clearly and as the dominant sound, so as to reduce background noise leakage. The voice detector may be comprised in the fluency aid or may be separate from the fluency aid.

Preferably, the audible sound may be a click or tone. Users of the fluency aid may prefer specific sounds to which to time their speech. A click or tone provides a clear sound, easily recognisable among other sounds. The timing and nature of the audible sound(s) may be programmable, based for example on which frequency (timing) and which type of sound aids the fluency of the user.

According to one or more examples, the fluency aid may further comprise a masking sound generator for generating a masking sound.

Masked Auditory Feedback (MAF) refers to the use of sound to mask the speaker's own voice. A masking sound may include any sound suitable for masking the user's own voice. In MAF a masking sound may be applied to the user's voice detected by a voice detector so as to be able to feedback to the user a feedback signal having a controllable amount of the user's voice and a controllable amount of the masking sound present. In an example the masking sound generator may be activated or deactivated by use of a switch.

According to one or more examples, the masking sound is faded out following detection of the voice.

For some users, it may be preferable that the masking sound is played at a constant, initial volume, which is then gradually reduced either partially or completely once they have started speaking. Since some stammerers only stammer when starting to speak, once they have started speaking the masking sound may be reduced in volume so that they can hear their own voice again. This fading out of the masking sound, once the user begins speaking (once the voice detector detects a voice), allows the user to adjust the volume of their own voice, based on their own auditory feedback, so as to speak normally (at a normal volume).

In an example, the masking sound may be played (output) at an initial volume (loudness) which is reduced over time such that the masking sound becomes gradually quieter. This is advantageous to users who wish to hear the masking sound before beginning to speak, but who wish for the masking sound, and the masking effect, to be reduced over time. A user may therefore choose when to begin speaking based on a remaining volume of the masking sound. As the masking sound is faded, the masking effect becomes reduced. Therefore, a user may prefer to begin speaking when their own voice is only partially masked.

Preferably, in an example, the masking sound includes at least one of white noise, pink noise, tones and music.

The masking sound may take any suitable form, for example white noise, pink noise, tones and/or music. These forms of masking sound may be selected based on user preference, based on effectiveness at relieving the user from the symptoms of stammering or based on the situation, for example if the user needs to hear people that they are speaking to.

In an example, the controller is further operable to control the pacing signal generator so as to cause the audible sound to continue for a predetermined amount of time.

It may be preferable to prevent the audible sound from being output, at regularly timed intervals, indefinitely. For example, in case the user has no intention of speaking and therefore does not require a fluency aid. Further, causing the audible sound to continue to be output, at regularly timed intervals, for a predetermined amount of time has the advantage of reducing power consumption.

Preferably, the pacing signal generator may be activated or deactivated by a switch.

The switch may be any suitable switch for this purpose. The user may notice themselves starting to stammer or may wish to speak without the fluency aid. Therefore a switch may be provided to activate and/or deactivate the pacing signal generator. The switch may for example have an ON state and an OFF state, wherein, based on the switch states, the pacing signal generator is switched on or off, respectively.

Preferably, the switch may be a hook-switch, an electronic hook-switch and/or a user-operated switch. A hook-switch or an electronic hook-switch are advantageous in that the user does not need to operate a switch themselves. For example, hook-switches are often found on telephones or headsets (headphones with a built-in microphone) and may switch on or off when a call is received, without separate user input. A user-operated switch is advantageous to give the user greater control over exactly when the pacing signal generator is activated or deactivated. These may be combined if, for example, the user wishes to make a call by a "hook-switch button".

In one example, the present disclosure may be embodied in noise cancelling headphones which include a hook-switch. To aid the user before speech has started the hook-switch is used to trigger generation of the audible sound which is output to the user. The hook-switch may be used to both enable and disable the audible sound or alternatively the hook-switch may be used to initiate the audible sound, which is then faded out as described above.

According to one or more examples, the fluency aid may further comprise a feedback signal generator for providing altered auditory feedback, AAF, based on the detected voice.

Altered Auditory Feedback is a technique for changing the information fed back to a person (for example a user of the fluency aid) in order to change or mask the person's perception of their own speech.

Preferably, in accordance with one or more examples, the altered auditory feedback, AAF, includes at least one of delayed auditory feedback, DAF, frequency altered feedback, FAF, and masked auditory feedback, MAF.

Delayed Auditory Feedback (DAF) refers to a technique whereby the speaker's voice is delayed before being presented to the speaker's ears. The level of improvement from stammering to fluency varies from user to user as does the long term effect. In cases where the user demonstrates a decreased effectiveness, altering the delay time has been reported to restore the effectiveness of DAF. The duration of the delay may for example lie in the range of 50-250 ms.

Frequency Altered Feedback (FAF) refers to a technique whereby the user's voice is shifted in frequency before being fed back to the user's ears. It is therefore also referred to as Frequency Shift Feedback (FSF). One approach is to shift the user's voice down one octave. The effectiveness of FAF on reducing stammering is similar to that of DAF. Some studies suggest FAF produces speech, closer to the user's normal speech, compared to MAF which tends to lead to louder speech and DAF which tends to lead to slower speech.

A combination of different forms of AAF provides an advantage of increased versatility and effectiveness to a broader range of stammerers and types of stammer.

Preferably, in an example, the audible sound is output at a loudness based on a loudness of the detected voice.

It may be preferable to a user for the audible sound to be output at a loudness level comparable to, quieter than or louder than the loudness of the detected voice, as desired.

According to one or more examples, the fluency aid may further comprise a background noise detector for detecting background noise around the fluency aid, wherein the audible sound is output at a loudness based on a loudness of the background noise.

A background noise detector may for example be a microphone. The background noise detector may be positioned so as to detect background noise, for example further away from the speech region in front of a user's mouth than the voice detector.

Preferably, the audible sound is output to both ears of a user.

Improved performance is achieved if the audible sound is replayed into both ears. For example, by providing the audible sound to both ears of a user, the sound heard by the user can be more accurately controlled, so as to improve the effect of the fluency aid.

According to an example of a further aspect there is provided a telephone, headphones, acoustic noise cancelling headphones, smart watch, or other portable device comprising the fluency aid as described above. These and any other wearable devices may include a fluency aid as described above.

BRIEF DESCRIPTION OF DRAWINGS

For a better understanding of the present disclosure, and to show how the same may be carried into effect, reference will now be made, by way of example only, to the accompanying drawings in which.

DETAILED DESCRIPTION

Figure 1:
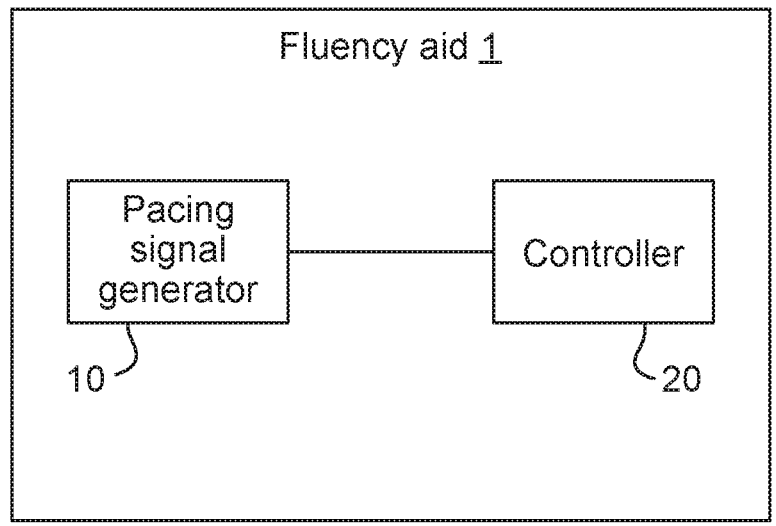
FIG. 1 is an example of a fluency aid according to the present disclosure.

Throughout this description any features which are similar to features in other figures have been given the same reference numerals.

The description below sets forth example fluency aids according to this disclosure. Further examples and implementations will be apparent to those having ordinary skill in the art. Further, those having ordinary skill in the art will recognize that various equivalent techniques may be applied in lieu of, or in conjunction with, the examples discussed below, and all such equivalents should be deemed as being encompassed by the present disclosure.

The arrangements described herein can be implemented in a wide range of devices and systems. However, for ease of explanation, an illustrative example will be described.

FIG. 1 illustrates a first example of a fluency aid 1 according to the present disclosure. As shown, a fluency aid 1 includes a pacing signal generator (pacing device) 10 and a controller 20. The pacing signal generator 10 is able to output a signal for generating an audible sound. The audible sound is output at regularly timed intervals to allow the user to speak with a regular rhythm. Based on a voice being detected by a voice detector, the controller 20 is operable to control the pacing signal generator 10 so that the output signal causes the audible sound to continue, stop or fade. The audible sound may preferably resemble a sound of a metronome. Further, the regular timing at which the audible sound is output may be programmable and/or adjustable, for example to a frequency showing increased fluency in the user.

In an example, the audible sound is output to a user and preferably to both ears of a user. For example, the audible sound may be provided to at least one speaker of a pair of headphones or to an earbud. The regularly timed intervals may preferably be set by a timer. The timer may, for example be included in the pacing signal generator 10 or may be separately disposed, but connected to, the pacing signal generator 10. The voice detector may be comprised in the fluency aid or may be separate from the fluency aid 1. The fluency aid 1 may further comprise a sound generator, such as a speaker, for generating the audible sound based on the signal output from the pacing signal generator 10.

In an example, the fluency aid 1, including the pacing signal generator 10, may be advantageously used by a person who has found that speaking in time with a regular beat aids fluency of speech. The pacing signal generator 10 may therefore be operable to output the regular beat, which is an example of an audible sound, as described above. The pacing signal generator 10 may be activated and deactivated by a switch.

Figure 2:
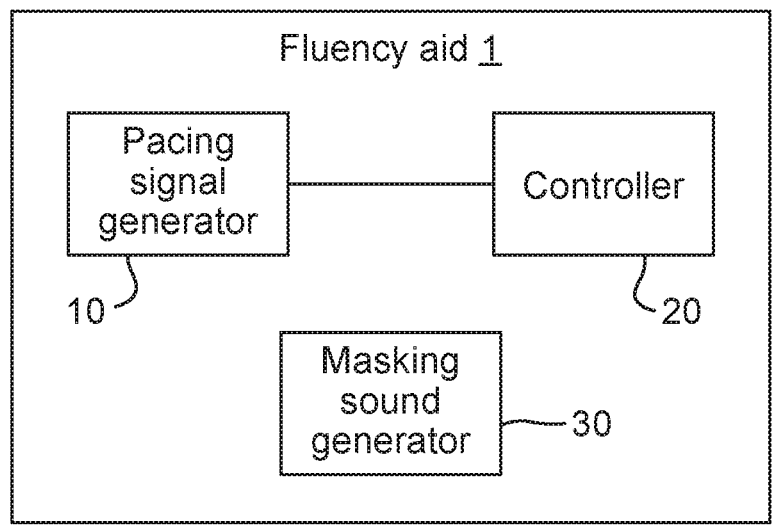
FIG. 2 is an example of a fluency aid according to the present disclosure further comprising a masking sound generator.

FIG. 2 illustrates a second example of a fluency aid 1 according to the present disclosure, wherein the fluency aid 1 further includes a masking sound generator 30. The masking sound generator 30 is operable to generate a masking sound. The masking sound may be faded out following detection of the voice by the voice detector. The masking sound may include at least one of white noise, pink noise, tones and music. The masking sound generator 30 may for example be, or include, a speaker or may be embodied in headphones.

Embodiments of the present aspects may be useful in circumstances where a person who suffers from stammering or other speech disorder wishes to speak to another person either in person or via a communication device such as a phone. Thus, the user may operate a fluency aid 1, such as the fluency aid described above with respect to FIGS. 1 and 3, which produces a regularly timed sound. Beneficially the regular sound helps the user start to speak and/or may aid the fluency of the user's speech. A fluency aid according to one or more examples may advantageously assist the user by generating the regularly timed beat before the user begins speaking, thus giving the user a rhythm with which to time their speech. In addition, according to one or more examples, the fluency aid may also be operable to emit an audible masking sound, which is able to partially or completely mask or obscure the user's voice from themselves.

The masking sound generator 30 may for example be part of a sound generator operable to output the regularly timed audible sound, or alternatively may be separate. Preferably, the masking sound and the audible sound are generated such that the masking sound obscures the user's own voice, but does not obscure the regularly output audible sound. A suitable masking sound may be selected for this purpose, such as pink noise or music having a complementary beat to the regularly output audible sound. In an example, the masking sound may be combined with the regularly output audible sound, for example in a sound generator, prior to being output to the user. Some users may prefer the masking sound to continue being generated while they speak. Alternatively, the masking sound may be faded, for users who benefit from the masking when starting to speak, but who prefer thereafter to be able to hear their own voice.

Figure 3:
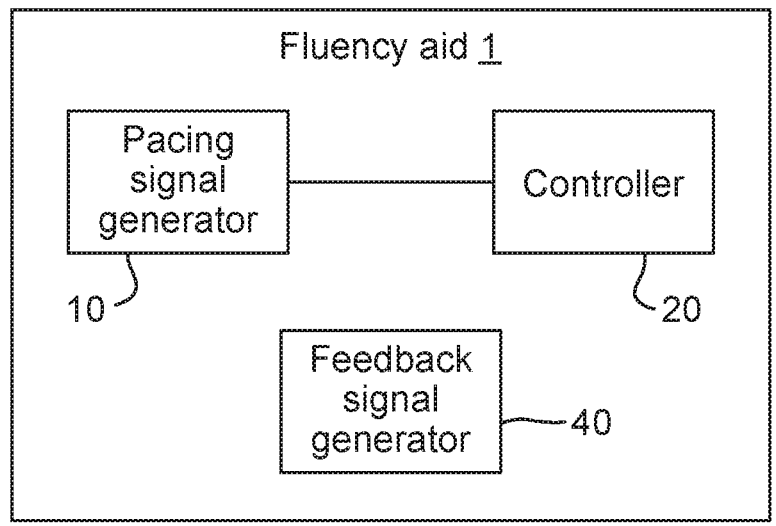
FIG. 3 is an example of a fluency aid according to the present disclosure further comprising a feedback signal generator.

FIG. 3 illustrates a third example of a fluency aid 1 according to the present disclosure, wherein the fluency aid 1 further includes a feedback signal generator 40. The feedback signal generator 40 is operable to provide or emit altered auditory feedback, AAF, based on a voice detected by the voice detector. The AAF provided by the feedback signal generator 40 may include at least one of delayed auditory feedback, DAF, frequency altered feedback, FAF, and masked auditory feedback, MAF, as described above.

In accordance with the example, the voice of the user, which may be detected by the voice detector, may be used to generate a voice signal which is output from the voice detector. The feedback signal generator 40 is then operable to alter the voice signal in order to provide AAF, based on the voice signal. Thus, one or more types of AAF are applied to the voice signal. The AAF may then be output, for example to the sound generator and, on the basis of the AAF generated by the feedback signal generator 40, the sound generator may generate AAF (an AAF sound), which may be output to the user.

Figure 4:
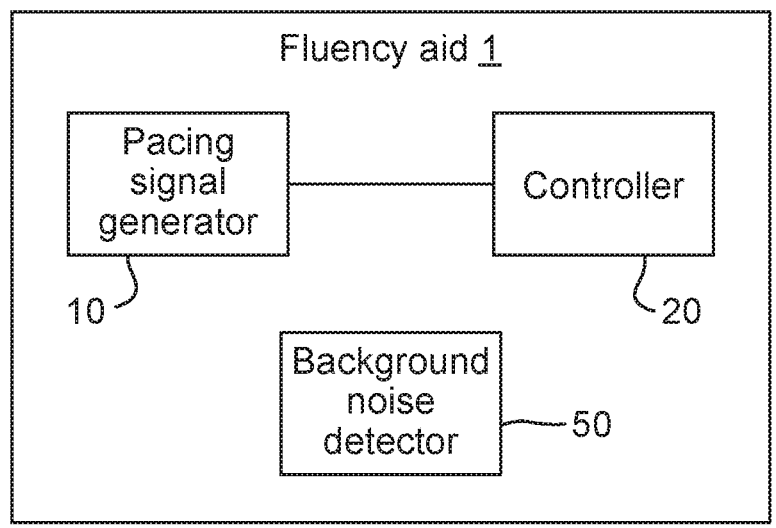
FIG. 4 is an example of a fluency aid according to the present disclosure further comprising a background noise detector.

FIG. 4 illustrates a fourth example of a fluency aid 1 according to the present disclosure, wherein the fluency aid 1 further includes a background noise detector 50. The background noise detector 50 is operable to detect background noise around the fluency aid. The audible sound may be output at a loudness based on a loudness of the background noise, detected by the background noise detector 50. The background noise detector 50 may for example be, or include, a microphone.

Figure 5A:
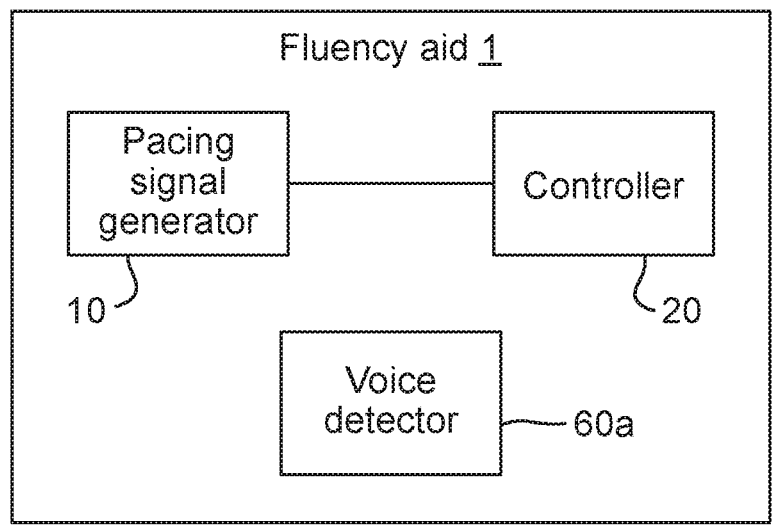
FIGS. 5a and 5b are examples of a fluency aid according to the present disclosure further illustrating a voice detector.

FIG. 5a illustrates a fifth example of a fluency aid 1 according to the present disclosure, wherein the fluency aid 1 further includes a voice detector 60a. The voice detector 60a is operable to detect a voice of a user.

The voice detector 60a may for example be, or include, a microphone. The voice detector 60a may preferably be positioned, in use, so as to be in a speech region in front of a user's mouth. Positioning the voice detector 60a in the speech region in front of a user's mouth provides the advantage that the voice detector 60a may detect the user's voice clearly and as the dominant sound, so as to reduce background noise leakage. The voice detector may be comprised in the fluency aid or may be separate from the fluency aid.

In addition, the voice detector may comprise signal processing operations which allow speech-like sounds to be identified. Thus, according to one example, sounds which are detected by the microphone of the voice detector will be converted into digital form for use by parts which implement digital signal processing operations upon signals that are derived from the microphone.

Figure 5B:
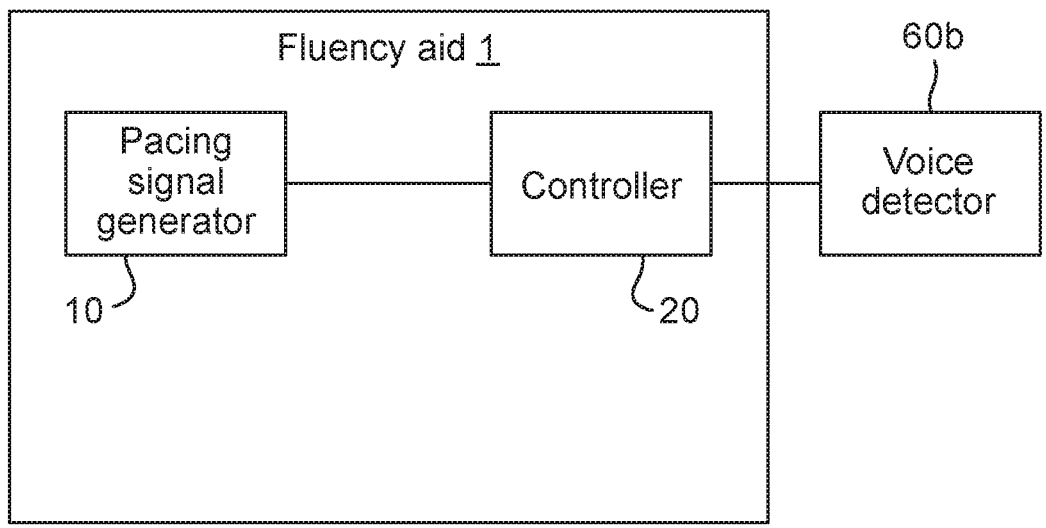

FIG. 5b illustrates a sixth example in which the voice detector 60b is separate to the fluency aid 1. In an example, the voice detector 60b may preferably be located close to the user's mouth, whereas the fluency aid 1 may be located closer to the user's ear.

The voice detector 60a, 60b may operate on the basis of detecting any sound at all or any sound pressure level (SPL) above a threshold level (e.g. a threshold loudness level). Such a threshold may be calibrated based on detected background sound levels. Alternatively, the voice detector 60a, 60b may be operable to recognise sounds resembling speech, for example speech patterns, or even a specific user's voice so as to distinguish the user's voice from the voices of other people speaking nearby.

When determining whether the user has started speaking, the voice detector 60a, 60b may require that speech is detected, in any of the ways described above, for a minimum amount of time. It may be beneficial to require a minimum amount of speech (require a user to be speaking for a minimum amount of time) before considering a voice as detected. This minimum amount of speech may be set as a few seconds of continuous speech or, if the voice detector 60a, 60b is able to recognise sounds resembling speech, may be set as one or more spoken words.

Any of the above-described examples may be included in a telephone, headphones, acoustic noise cancelling headphones, smart watch, or other portable or wearable device.

It will be appreciated that features of any of the above aspects and examples may be provided in any combination with the features of any other of the above aspects and examples.

The fluency aid may be at least partly implemented within a speaker housing. The housing may be, e.g. that of a wired or wireless headset, an ear-bud, a supra-aural headphone or a speaker portion of a mobile device such as a mobile phone handset. Alternatively, the parts associated with one or more features of the fluency aid may be provided in an apparatus separate to the apparatus that comprises the at least one speaker. For example, the fluency aid may be at least partly implemented within a mobile handset or a "dongle", wherein a wired or wireless connection is provided between the apparatuses. According to one implementation the switch and/or the voice detector are provided in an apparatus that is separate from the apparatus, e.g. headset or ear-bud.

It should be noted that the above-mentioned examples illustrate rather than limit the disclosure, and that those skilled in the art will be able to design many alternative configurations without departing from the scope of the appended claims. The word "comprising" does not exclude the presence of elements or steps other than those listed in a claim, "a" or "an" does not exclude a plurality, and a single feature or other unit may fulfil the functions of several units recited in the claims. Any reference numerals or labels in the claims shall not be construed so as to limit their scope. The features of any dependent claim may be combined with the features of any of the independent claims or other dependent claims.

The invention claimed is:

1. A fluency aid comprising:
   a pacing signal generator operable to output a signal for generating, at regular time intervals, an audible sound;
   a controller operable, in response to a voice being detected by a voice detector, to control the pacing signal generator such that the output signal causes the audible sound to continue for a predetermined amount of time, stop or fade;
a background noise detector for detecting background noise around the fluency aid, wherein the audible sound is output at a loudness based on a loudness of the background noise; and
a masking sound generator for generating a masking sound, wherein the masking sound is faded out following detection of the voice.

2. The fluency aid according to claim 1, wherein the audible sound is a click or tone.

3. The fluency aid according to claim 1, wherein the masking sound includes at least one of white noise, pink noise, tones and music.

4. The fluency aid according to claim 1, wherein the pacing signal generator is activated or deactivated by a switch.

5. The fluency aid according to claim 4, wherein the switch is a user-operated switch.

6. The fluency aid according to claim 1, further comprising:
   a feedback signal generator for providing altered auditory feedback, AAF, based on the detected voice.

7. The fluency aid according to claim 6, wherein the altered auditory feedback, AAF, includes at least one of delayed auditory feedback, DAF, frequency altered feedback, FAF, and masked auditory feedback, MAF.

8. The fluency aid according to claim 1, wherein the audible sound is output at a loudness based on a loudness of the detected voice.

9. The fluency aid according to claim 1, wherein the audible sound is output to both ears of a user.

10. A telephone, headphones, acoustic noise cancelling headphones, smart watch, or other portable device comprising the fluency aid according to claim 1.

* * * * *